United States Patent [19]
Nardella et al.

[11] Patent Number: 5,941,876
[45] Date of Patent: Aug. 24, 1999

[54] ELECTROSURGICAL ROTATING CUTTING DEVICE

[75] Inventors: Paul C. Nardella, Wareham; John F. Cvinar, Winchester; Thomas A. Wrublewski, Sharon, all of Mass.

[73] Assignee: Medical Scientific, Inc., Taunton, Mass.

[21] Appl. No.: 08/803,170

[22] Filed: Feb. 19, 1997

Related U.S. Application Data

[60] Provisional application No. 60/013,251, Mar. 11, 1996.

[51] Int. Cl.$^6$ ........................................ A61B 17/32
[52] U.S. Cl. ........................ 606/45; 606/49; 606/170; 606/180; 604/22
[58] Field of Search .................... 606/41, 42, 45–50, 606/170, 180; 604/21, 22

[56] References Cited

U.S. PATENT DOCUMENTS

| | | |
|---|---|---|
| 3,945,375 | 3/1976 | Banko . |
| 4,016,881 | 4/1977 | Rioux et al. . |
| 4,532,924 | 8/1985 | Auth et al. . |
| 4,637,390 | 1/1987 | Sorochenko . |
| 4,657,017 | 4/1987 | Soronchenko . |
| 4,674,499 | 6/1987 | Pao . |
| 4,802,476 | 2/1989 | Noerenberg et al. . |
| 4,842,578 | 6/1989 | Johnson et al. . |
| 4,917,082 | 4/1990 | Grossi et al. . |
| 5,037,379 | 8/1991 | Clayman et al. . |
| 5,047,027 | 9/1991 | Rydell . |
| 5,080,660 | 1/1992 | Buelna . |
| 5,122,138 | 6/1992 | Manwaring . |
| 5,133,713 | 7/1992 | Huang et al. . |
| 5,176,677 | 1/1993 | Wuchinich . |
| 5,192,280 | 3/1993 | Parins . |
| 5,197,964 | 3/1993 | Parins . |
| 5,201,731 | 4/1993 | Hakky . |
| 5,217,458 | 6/1993 | Parins . |
| 5,217,478 | 6/1993 | Rexroth . |
| 5,269,780 | 12/1993 | Roos . |
| 5,269,782 | 12/1993 | Sutter . |
| 5,269,794 | 12/1993 | Rexroth . |
| 5,282,799 | 2/1994 | Rydell . |
| 5,290,282 | 3/1994 | Casscells . |
| 5,290,303 | 3/1994 | Pingleton et al. . |
| 5,304,124 | 4/1994 | Essig et al. . |
| 5,318,564 | 6/1994 | Eggers . |
| 5,318,589 | 6/1994 | Lichtman . |
| 5,324,289 | 6/1994 | Eggers . |
| 5,330,471 | 7/1994 | Eggers . |
| 5,364,395 | 11/1994 | West, Jr. . |
| 5,391,166 | 2/1995 | Eggers . |
| 5,403,312 | 4/1995 | Yates et al. . |
| 5,411,514 | 5/1995 | Fucci et al. . |
| 5,423,844 | 6/1995 | Miller ................................ 606/171 |
| 5,441,499 | 8/1995 | Fritzsch . |
| 5,445,638 | 8/1995 | Rydell et al. . |
| 5,456,689 | 10/1995 | Kresch et al. . |
| 5,480,397 | 1/1996 | Eggers et al. . |
| 5,484,435 | 1/1996 | Fleenor et al. . |
| 5,492,527 | 2/1996 | Glowa et al. . |
| 5,527,331 | 6/1996 | Kresch et al. . |
| 5,531,677 | 7/1996 | Lundquist et al. . |
| 5,569,244 | 10/1996 | Hahnen . |
| 5,571,100 | 11/1996 | Goble et al. . |
| 5,697,281 | 12/1997 | Eggers et al. . |
| 5,697,536 | 12/1997 | Eggers et al. . |
| 5,697,882 | 12/1997 | Eggers et al. . |
| 5,697,909 | 12/1997 | Eggers et al. . |

FOREIGN PATENT DOCUMENTS

| | | |
|---|---|---|
| 0596436 A1 | 5/1994 | European Pat. Off. . |
| 9611638 | 4/1996 | WIPO . |
| 9624296 | 8/1996 | WIPO . |

*Primary Examiner*—Michael Peffley
*Attorney, Agent, or Firm*—Nutter, McClennon & Fish, LLP

[57] ABSTRACT

An electrosurgical apparatus includes a rotary, tissue affecting device in the form of one or more rotating blades, a rotating drill, or a rotating shaving/abrading device that serves as an active, energy delivering electrode. The active electrode effectively cuts tissue at the surgical site without relying solely upon the mechanical cutting action of the tissue affecting device. The rotary surgical device can be in a form such that it is suitable for use in open or closed surgery.

18 Claims, 4 Drawing Sheets

(b)

(c)

(d)

|     | ADD | ADC | SHL | ROL | SHR | ROR |
|-----|-----|-----|-----|-----|-----|-----|
| (a) | M2  | M2  | M3  | M3  | M4  | M1  |
| (b) | -   | -   | M3  | M2  | M1  | M1  |
| (c) | M4  | M2  | M3  | M3  | M1  | M1  |
| (d) | M1  | M1  | M2  | M2  | M3  | M3  |

ELECTROSURGICAL ROTATING CUTTING DEVICE

RELATED APPLICATIONS

This application claims priority under 35 U.S.C. §119(e) from application Ser. No. 60/013,251 filed Mar. 11, 1996.

GOVERNMENT RIGHTS

Not applicable.

BACKGROUND OF THE INVENTION

Rotating surgical instruments that mechanically cut, shave, abrade and drill hard or soft tissue are well known in the art and have proven, over time, to be quite useful. Such tools can be used in open or closed surgical procedures to remove affected tissue. Typical rotating instruments used in these procedures include surgical drilling instruments, such as bone drills, and other rotating mechanical cutting and shaving devices, such as morsellators and power shavers.

Conventional power shavers include an inner rotatable drive shaft having an abrading element at a distal end. The drive shaft seats within a central lumen of the shaver housing such that the abrading element is exposed at the distal end. The drive shaft couples to a motor which imparts rotary movement to the shaft. The power shaver mechanically cuts or shaves affected tissue by the direct mechanical contact of the abrading element with the tissue.

One drawback of such devices is that the abrading edge of the instrument must be extremely sharp to enable effective mechanical cutting of the tissue. During the course of the surgical procedure, however, the abrading or cutting edge of the rotating tool tends to dull, thereby decreasing the cutting performance of the tool. When this occurs, the cutting tool must be replaced. The need for frequent replacement of the abrading portion of the device increases the overall time necessary to conduct the surgical procedure while concomitantly increasing the cost of delivering the medical services and in stocking the replacement components for the medical device.

There thus exists a need in the art for rotary surgical devices that are able to provide effective cutting and abrading of tissue while minimizing or eliminating the need to replace selected components, such as the abrading element, of the device.

SUMMARY OF THE INVENTION

The present invention pertains to an electrosurgical apparatus that includes a rotary, tissue affecting device in the form of one or more rotating blades, a rotating drill, or a rotating shaving/abrading device that serves as an active, energy delivering electrode. The active electrode effectively cuts tissue at the surgical site without relying solely upon the mechanical cutting action of the tissue affecting device. The rotary surgical device can be in a form such that it is suitable for use in open or closed surgery. The term "closed surgery" is intended to include arthroscopic, endoscopic, hysteroscopic, laparoscopic, and resectoscopic surgical techniques. Closed surgical techniques typically utilize elongated instruments which are inserted into the patient's body through a small incision or a natural oriface, to allow a secondary instrument easy access to the surgical site. A variety of such surgical devices are well known in the art and are well described in the patent literature. Representative devices are described in U.S. Pat. No. 4,842,578 (Johnson et al.), U.S. Pat. No. 5,411,514 (Fucci et al.) and U.S. Pat. No. 5,492,527 (Glowa et al.).

In its basic configuration, the electrosurgical device of the present invention includes a rotating, tissue affecting device having a distal, tissue contacting end which serves as an active, energy delivering electrode suitable for cutting tissue. The actual shape and structure of the device will depend upon the purpose for which the device is used. For example, rotating cutting devices and arthroscopic shaving devices are well known in the art and the structure of such devices can be assumed. The rotating, tissue affecting device also includes a proximal end, usually in the form of an elongate drive shaft, which fits within a chuck or holder assembly. The holder assembly is then mounted to the base portion of an outer cannula that can include one or more electrically conductive contacts. The cannula can form part of an arthroscope, endoscope, hysteroscope, laparoscope, or resectoscope as is well known in the art.

The electrical contact is electrically connected at one end to one pole of a remote electrosurgical generator and at the other end to the elongate drive shaft of the tissue affecting device. The contact energizes the rotating shaft and thus the distal abrading end by transferring cutting energy from the electrosurgical generator to the drive shaft. Preferably, the rotating, tissue affecting device is coated with a non-conductive material (e.g., Teflon or Kynar) along an intermediate portion disposed between the area of the drive shaft that bears against the contact and the distal abrading end to electrically isolate the rotating device from the outer cannula.

The rotating electrosurgical device of the invention may be utilized in a monopolar or bipolar mode. When used in the monopolar mode the distal end of the rotating, tissue affecting device serves as the active, energy delivering electrode. The electrical circuit is completed by attaching a remote ground pad which serves as a return electrode to the patient's body, such as to the thigh or back.

When used in the bipolar mode the rotating, tissue affecting device again serves as the active, energy delivering electrode. One or more local electrodes, serving as the return electrode, are associated with, in proximity to or comprise the distal end of the housing that is disposed adjacent to the rotating, tissue affecting device. It is understood that one or more active electrodes may be used in the bipolar mode.

During closed surgical procedures it is typically necessary to supply a fluid to a surgical site in order to distend the surgical area and to improve visibility for the surgeon. If a monopolar surgical system is to be used in a closed surgical procedure the fluid medium is typically non-ionic, otherwise the current generated by the active electrode will be dispersed by the medium, thus requiring the use of higher voltage and current levels. The use of higher voltages to deliver an appropriate level of current to effect tissue cutting subjects the patient to increased risks of harm. Specifically, the use of higher voltage levels can inadvertently harm tissue unrelated to the surgical procedure. The use of non-ionic fluid poses additional surgical risks, such as those associated with the inadvertent introduction of excess non-ionic fluid into the blood stream. The absorbed non-ionic solution can create dangerous electrolytic disturbances within the patient, which can lead to cardiac arrhythmia, brain swelling and even sudden death.

Bipolar systems tend to be more advantageous since an isotonic solution (e.g., saline or Ringer's solution) can be used to distend the surgical site, rather than a non-ionic solution. The patient, therefore, is not exposed to potentially harmful levels of current since the isotonic medium does not disperse the current at the tip of the active electrode throughout the medium. Furthermore, the introduction of the isotonic solution into the patient's bloodstream does not create the dangerous electrolytic imbalances associated with absorption of the non-ionic solution.

The return electrodes typically are mounted on a distal, tissue contacting edge of the housing that forms the outer cannula. Alternatively, the return electrodes can be mounted on the distal end of a separate sheath that is mountable over the outer surface of the cannula that forms part of the arthroscope, endoscope, hysteroscope, laparoscope or resectoscope. This bipolar configuration is preferably used in closed surgical applications which employ ionic solutions.

BRIEF DESCRIPTION OF THE DRAWINGS

The invention may be more fully understood from the following detailed description in combination with the drawings in which:

FIG. 1A is an enlarged view of a portion of a tissue affecting device shown in FIG. 1;

FIG. 2A is an enlarged view of a portion of the tissue affecting device shown in FIG. 2;

DESCRIPTION OF THE PREFERRED EMBODIMENTS

Figure 1:
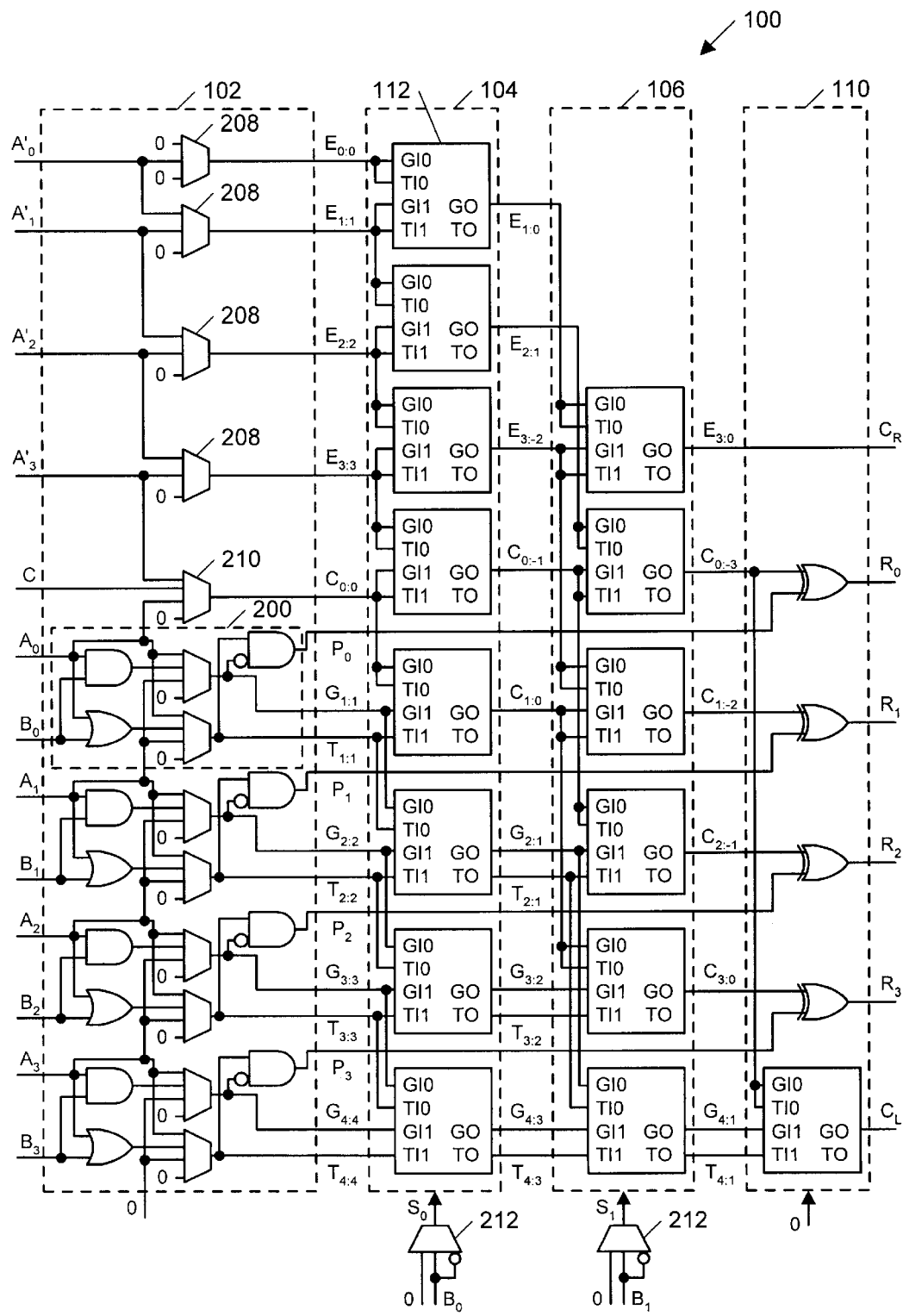
FIG. 1 is an exploded view of a first embodiment of an electrosurgical device according to the present invention.

Referring now to FIGS. 1 and 1A in which like elements are provided having like reference designations, an electrosurgical device 10 is shown to include a rotary, tissue affecting element 12 and an outer cannula 14. The tissue affecting element 12 serves as an active, energy delivering electrode, as is described in further detail below.

The tissue affecting element 12 includes a rotatable shaft portion 16 that is mounted within a chuck or holder assembly 18. The shaft 16 includes a distal end 16B and a proximal end 16A that is secured within a first receiving end 18A of the holder assembly. As illustrated, the shaft portion 16 can be in the form of an auger bit having a single spiral groove that extends from the proximal end 16A to the distal abrading end 16B. The auger bit is preferably coated with or encompassed by a non-conductive material between the proximal end 16A and the distal end 16B to electrically isolate the shaft from the outer cannula 14 when disposed therein. The distal abrading end 16B is preferably scored 20, i.e., the conductive coating is removed, at one or more locations to expose the electrically conductive material therebeneath. The illustrated score marks 20, shown in FIG. 1A, form an electrosurgical abrading edge when the electrically conductive shaft is connected to an electrosurgical generator, as discussed in further detail below. The electrosurgical abrading edge delivers electrosurgical energy (e.g., radio frequency (RF)) energy to tissue.

The illustrated auger bit is preferably used when the affected tissue at the surgical site comprises relatively firm tissue. This device type is preferred since the auger bit presents a relatively large cutting surface to the tissue.

The one-piece holder assembly 18 of the tissue affecting element 12 preferably includes flanged portion 22 which forms part of the first receiving end 18A, and a second axial hub portion 26. The hub portion 26 typically has a diameter that is larger than the neck 22A of the flanged portion 22. Preferably hub portion 26 includes a suction aperture 24 that extends transversely through the hub portion. The hub portion 26 terminates in a fluted extension 28 that is captured within a spring loaded cap assembly 30. The cap assembly is known in the art and includes an outer cylindrical body that has secured therein a tension spring (not shown). The fluted portion 28 preferably includes a radially outwardly-extending flange (not shown) which seats within and is captured by the spring loaded cap assembly 30. The cap assembly 30 is preferably sized to seat within the rotor portion of a conventional drive motor handle, such as that manufactured by Concept, Inc., of California, U.S.A. The fluted portion 28 further includes an axially extending (to the left in FIG. 1) base tab that is adapted to seat within a corresponding U-shaped seat within the motor handle. The drive motor handle preferably imparts a rotary motion to the holder assembly 18, thus rotating the shaft portion 16 of the tissue affecting element 12. The cap assembly 30 resiliently and telescopically moves along the longitudinal axis 32 of the shaft 16 to prevent endplay and runout of the drive mechanism of the motor handle from being transferred to the shaft 16 during operation.

Figure 2:
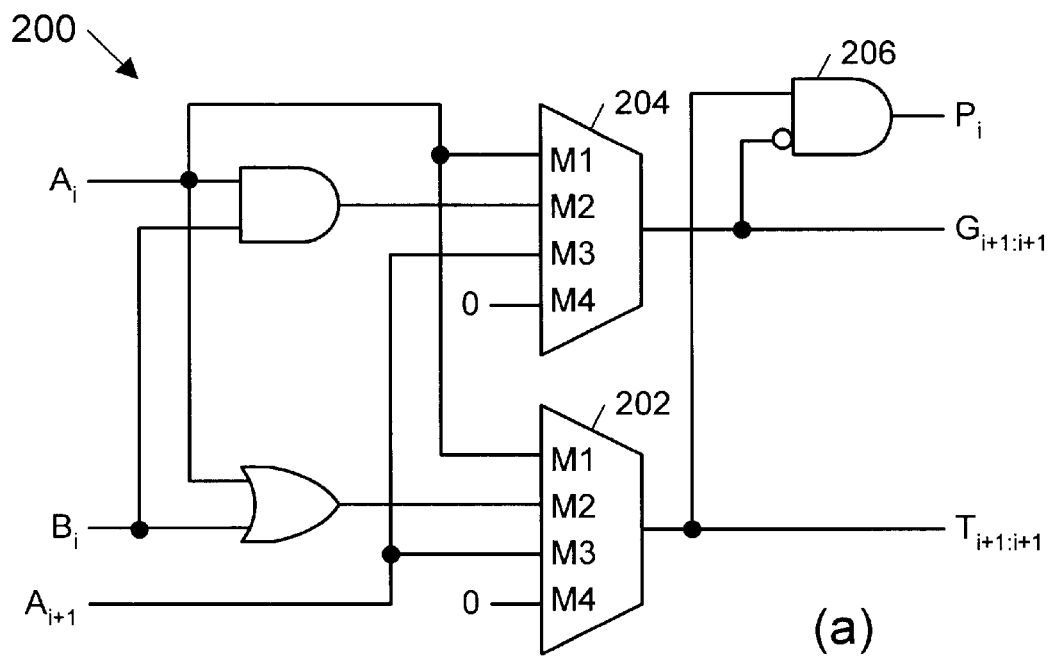
FIG. 2 is a cross-sectional view of another embodiment of a tissue affecting device according to the present invention.
Figure 2:
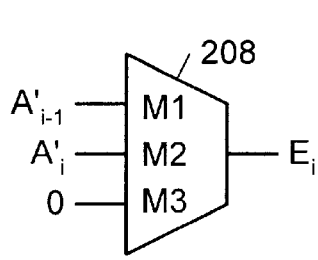
Figure 2:
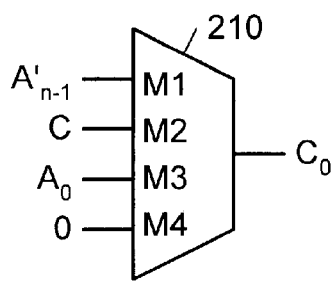
Figure 2:
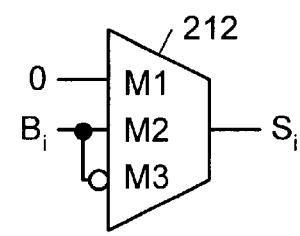
Figure 3:
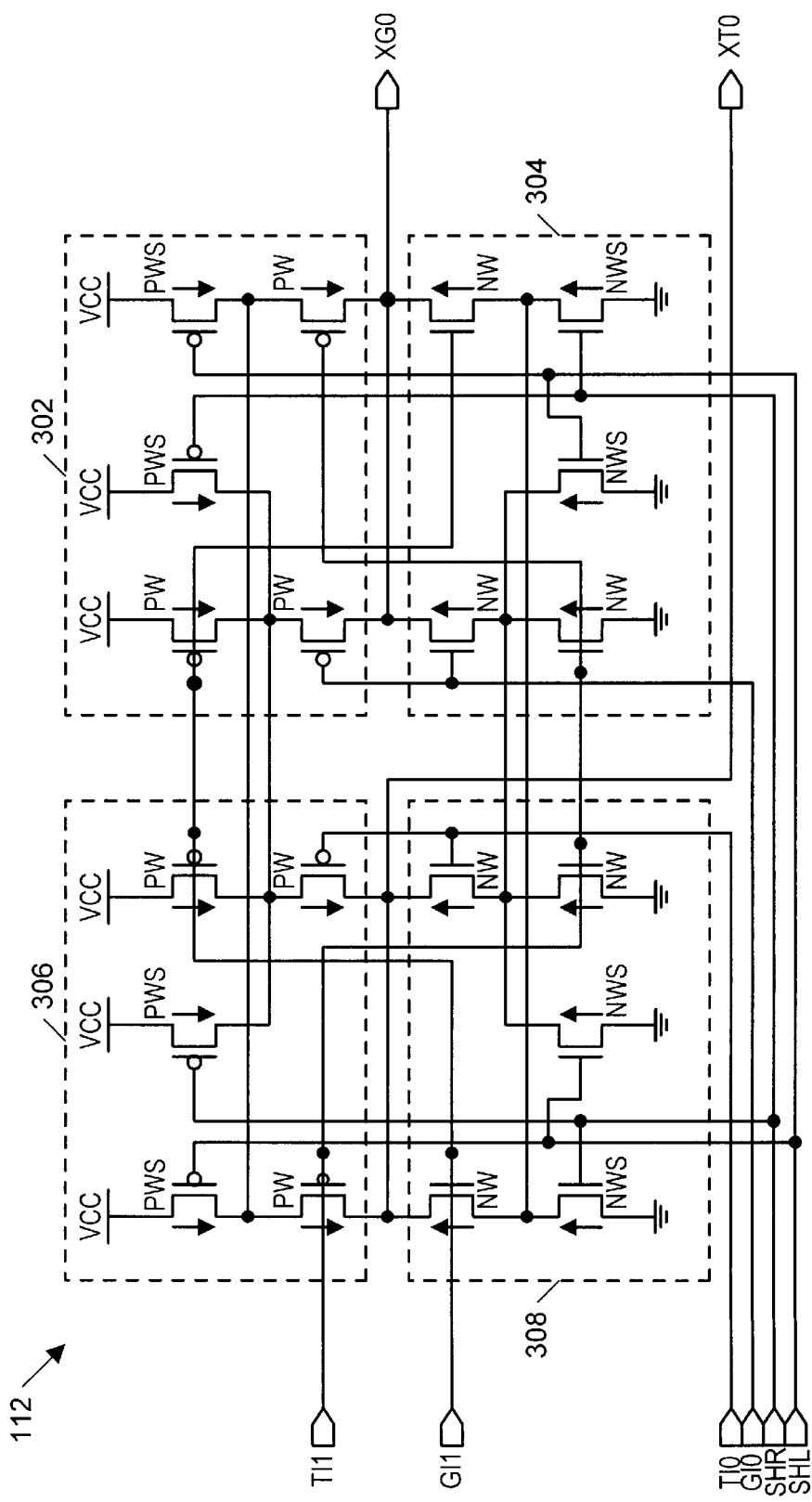
FIG. 3A is a side view of a portion of the electrosurgical cutting device shown in FIG. 1.
FIGS. 3B and 3C are a series of cross sectional views of an electrosurgical deivce according to the present invention.

FIG. 2 illustrates a second embodiment of the tissue affecting device 36 according to the present invention. Identical parts will be designated throughout the views by like reference numerals plus a superscript prime. The device 36 includes a shaft portion 38 that is mounted within a holder assembly 18'. The shaft portion 38 includes a substantially cylindrical outer body 38A that defines a central lumen 40. A proximal end 38B of the shaft 38 seats within the first receiving end 18A' of the holder assembly 18'. The lumen 40 extends along longitudinal axis 32 and is preferably in fluid communication with the suction aperture 24' formed in the hub portion 26'. This specific fluid arrangement allows the electrosurgical device 10 to remove fluid and tissue debris from the surgical site by applying a vacuum to the suction aperture 24'. The applied vacuum draws fluid and debris through the central lumen 40 and the aperture 24' and thus away from the surgical site.

The tissue affecting device 36 further includes a distal abrading end 38C having a serrated opening 42 that communicates with the central lumen 40. The shaft 38 is preferably covered by or coated with a non-conductive material between the proximal end 38B and the abrading end 38C to electrically isolate the shaft from the outer cannula 14. The illustrated abrading end 38C is preferably free of any insulating material to allow the shaft to function as an active, energy delivering electrode when energized by an electrosurgical generator.

The tissue affecting device 36 thus forms a simple and elegant cutting surface that is preferably used when the affected tissue at the surgical site comprises relatively soft tissue.

Those of ordinary skill will appreciate that alternative shaft designs can be used in conjunction with the teachings of the present invention. For example, the shaft can have a burr welded on the distal end of the shaft, which serves as an RF abrading end. Other designs can include the formation of a dremel head on the distal end of the shaft. The dremel head embodiment is preferably used when the affected tissue comprises ultrafirm tissue. As illustrated in FIG. 2, the shaft of the tissue affecting device can also include a central lumen to allow the removal of liquid and tissue debris from the surgical site. According to another practice, the auger bit design of FIG. 1 can be used to remove fluid and tissue debris from the surgical site by the rotating action of the shaft 16. The specific design of the shaft and abrading end are not critical features of the present invention, provided that the shaft includes an abrading end having a selected surface free of insulation to form a relatively high current density RF cutting edge.

With reference to FIGS. 1 and 3A–3C, the outer cannula 14 includes a base portion 48 that mounts an elongate outer sheath 50. The sheath 50 extends entirely or partly through a mounting bore 52, and preferably terminates prior to the commutator 60. The outer sheath 50 has a central lumen 62 that extends between a proximal end 50A which seats within bore 52 and a distal end 50B. The central lumen 62 preferably has a diameter slightly larger than the diameter of the shaft 16 of the tissue affecting element 12 to allow the shaft 16 to fit easily therein. The outer sheath 50 further includes an opening 64 formed in the distal end 50B. The opening 64 exposes the abrading end 16B of the shaft 16 to the tissue at the surgical site to effect tissue cutting during use.

An insulation material 66, e.g., a non-conductive coating, covers the outer portion of the sheath 50 between the proximal and distal ends 50A, 50B. Although not illustrated, it is understood that a non-conductive coating or material may be applied to the inner portion of sheath 50 as well. In one embodiment, the distal end 50B of the sheath 50 is exposed, i.e., is free of the non-conductive coating, and thus may serve as a return electrode when the electrosurgical device 10 is operated in the bipolar mode. Those of ordinary skill will appreciate that the electrosurgical device 10 can also operate without the non-conductive layer.

The base portion 48 of the outer cannula 14 includes a central bore 52 that extends between first and second ends 56A, 56B. The base portion 48 further includes a second bore having an aperture 54, illustrated in FIG. 3A, which extends into the base portion 48 and which communicates with bore 52. In a preferred embodiment, a longitudinal axis of the second bore is transverse to a longitudinal axis of bore 52. The transverse aperture 54 seats the commutator 60, which communicates the RF energy between the electrosurgical generator and the tissue affecting element. The commutator 60 preferably includes a resilient steel J-wire 68 that is electrically coupled to an electrically conductive button portion 70. According to one preferred embodiment, the J-wire 68 bears against the conductive outer portion of the rotary shaft 16 axially below, i.e., to the left in FIG. 1, the non-conductive coating 66 disposed on the sheath. The button portion 70 forces the J-wire 68 into contact with the shaft 16 to maintain electrical contact with the shaft 16 during operation. The operation of commutators are known in the art and need not be described further.

The base portion 48 also includes a first electrical port 72 that is adapted to seat a corresponding electrical lead which is coupled to the active output of the electrosurgical generator (not shown). The electrical port 72 is also electrically coupled to a conductive tab 74, which in turn is electrically coupled to the button portion 70 of the commutator 60. The electrical circuit pathway formed by the mating engagement of the J-wire 68, the button portion 70, the tab 74, and the electrical port 72 energizes the shaft 16, thus forming the active energy-delivering electrode of the invention.

The base 48 further includes an electrically conductive clip 78 that substantially surrounds and engages the outer sheath 50 below the non-conductive coating 66. The clip 78 is electrically coupled to a second electrical port 80 that is adapted to seat the other electrical lead of the electrosurgical generator. The conductive clip 78 and the port 80, in conjunction with the outer sheath 50, form the current return pathway for the electrosurgical device when operated in the bipolar mode.

With further reference to FIGS. 1 and 3A–3C, the first end 56A of the base portion 48 can have a conically shaped cavity 82 that tapers inwardly towards a second axially spaced cavity 84. The conically shaped cavity 82 is preferably shaped complementary to the hub portion 26 of the holder assembly. Specifically, the conically shaped cavity 82 includes a shoulder 82A that bears against the sloped front portion 26A when the tissue affecting element 12 is disposed within the outer cannula 14. The second cavity 84 is preferably configured to seat the flanged portion 22 of the holder assembly 18. In the illustrated embodiment, the flanged portion 22 of the element 12 is retained within the base 48 by the mating engagement of the flange 22 with the sloped and chamfered end 84A of the second axial cavity 84. This mating engagement prevents the tissue affecting device from dislodging from the outer cannula 14 during use.

The rotary electrosurgical device 10 of the invention can be assembled by inserting the shaft 16 of the tissue affecting element 12 within the central lumen 62 of the outer cannula 14. The holder assembly 18 is secured within the base 48 of the outer cannula 14 by the mating engagement of the flanged portion 22 of the holder assembly 18 with the sloping and chamfered end of cavity 84, as well as the engagement between the sloping surface 26A of the hub portion 26 which bears against the shoulder 82A of the cavity 82. In this position, the rotatable shaft 16 contacts the resilient J-wire 68 of the commutator 60. The outer cannula thus functions as the carrier for the tissue affecting element 12 of the present invention.

Once the tissue affecting element 12 is secured within the outer cannula 14, the entire assembly is secured to the drive handle motor by inserting the protruding cap assembly 30 and the hub portion 26 into the receiving end of the handle. The base tab formed on the end of the fluted section 28 slides between a corresponding U-shaped seat within the motor handle. The drive motor, when actuated, imparts a rotary motion to the tab and thus the shaft portion 16 of the tissue affecting device.

In the embodiment of FIG. 1, the distal abrading end 16B of the shaft aligns with the opening 64 formed in the distal end 50B of the outer sheath 50. This opening allows the rotary, tissue affecting element 12 to contact and thus act upon tissue at the surgical site.

Figure 3A:
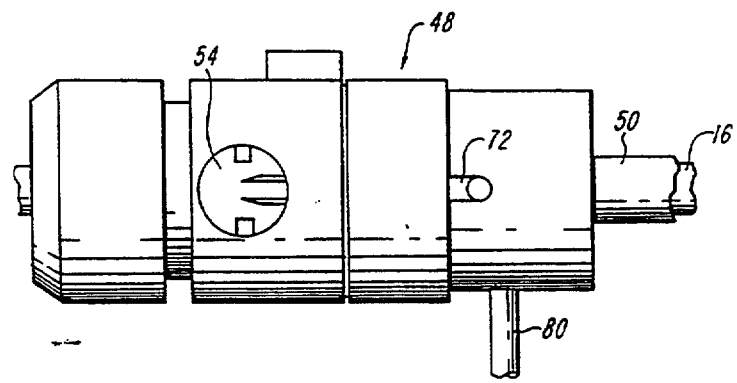
Figure 3B:
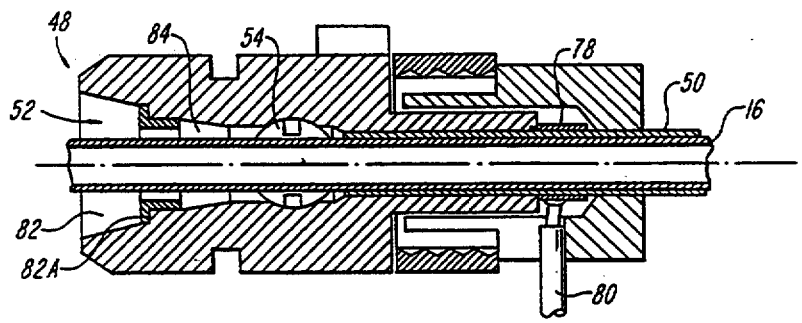
Figure 3C:
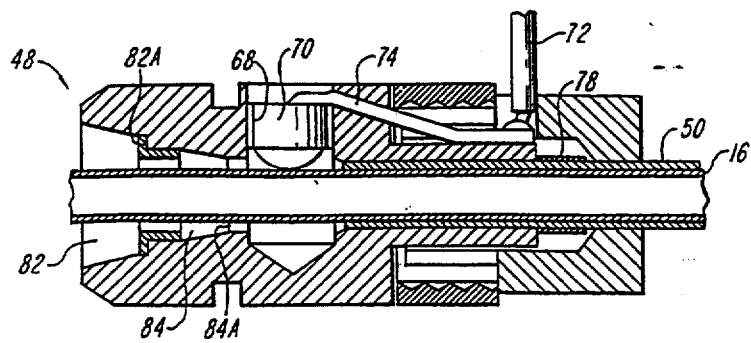

The electrical leads of the generator are connected to one or both of the electrical ports depending upon the selected mode of operation. For example, in the monopolar mode, the electrical lead associated with the active output of the generator is connected to the electrical port 72. This electrical connection energizes the shaft and thus forms an active rotary electrode, as illustrated in FIGS. 1 and 3C. A remote ground pad is secured to the patient to complete the electrical circuit. Alternatively, the other electrical lead associated with the generator can be coupled to the second electrical port 80 to form a bipolar rotary electrosurgical instrument in which an exposed (i.e., non-insulated) portion of sheath 50 serves as the return electrode.

A vacuum line can be connected to an appropriate pressure fitting formed on the drive motor handle to remove tissue and fluid from the surgical site. The pressure fitting of the drive motor is preferably in fluid communication with the suction aperture 24 formed in the hub portion 26 of the tissue affecting element 12. The aperture 24 in turn is in fluid communication with the central lumen 62 of the device and/or with the central lumen 40 of the tissue affecting device of FIG. 2. Consequently, a vacuum applied to the pressure fitting draws tissue debris through the central lumen and aperture and thus away from the surgical site.

In operation, the shaft 16 of the tissue affecting device is energized by actuating the electrosurgical generator. The rotatably actuable cutting element 16 is preferably coated over a substantial portion of its length with an insulating material. Preferably only the tissue contacting cutting edges of the abrading end remain uncoated of the insulating material, thus forming an active, energy delivering electrode. In one embodiment, the electrosurgical energy supplied by the generator is communicated through nearly the entire length of the rotating cutting element to the abrading end.

The shaft 16 of the element 12 is rotatably actuable by activating the drive-motor handle, which imparts a rotary motion to the shaft 16. As the shaft portion of the rotatable cutting element rotates, it is maintained in contact with a suitable electrical contact, e.g., J-wire 68, thus communicating electrosurgical energy supplied by the remote generator to the abrading end of the device.

In the embodiment of FIG. 1, the scored ends 20 of the tissue affecting device form an electrode that delivers radio frequency (RF) energy to target tissue. As the shaft 16 of the element 12 rotates, the movement of the energized abrading end towards the outer sheath creates a high energy arc discharge that serves to sever tissue at the surgical site. The excised tissue can be removed from the site through the lumen 62 of the cannula by the continuous rotary motion of the auger-bit type shaft 16. When the excised tissue reaches the holder assembly 18, the vacuum force applied to the drive motor handle draws the tissue through the suction aperture 24 and handle, and to a remote collection site.

The exposed outer portion of the sheath serves as the return electrode and thus completes the electrical circuit pathway necessary to properly dissipate the electrosurgical energy applied to the surgical site by the active electrode. Alternatively, the electrical lead of the generator which is coupled to the second electrical port 80 is disengaged and a remote ground pad is secured to the patient. The ground pad completes the circuit pathway and serves as the return electrode.

In the bipolar mode, the foregoing rotary electrosurgical device is configured such that the active and return electrodes are electrically isolated from each other. Specifically, the rotating shaft of the tissue affecting device, which is made from a conductive material, is coated or covered over virtually all of its length with an insulating material to electrically isolate the shaft from the outer sheath of the cannula 14. The shaft is then disposed in electrical communication with the active pole of the electrosurgical generator by way of the J-wire electrical contact 68, or a similar means.

If the tissue affecting device 36 of FIG. 2 is mounted within the outer cannula 14, the exposed serrated end of the device 36 serves as the active energy-delivering electrode. In this embodiment, the shaft 38 of the tissue affecting device 36 is actuated by activating the drive-motor handle. The movement of the positively energized abrading end 38C towards the isolated outer sheath 50 creates a high energy arc discharge that serves to incise tissue at the surgical site.

Hence, as the shaft 38 rotates, the tissue affecting device 36 cuts tissue by the mechanical action of the abrading end and by the electrosurgical energy (e.g., RF energy) delivered to the tissue by the energized cutting edge. The tissue cut by the device 36 is then removed from the surgical site via the central lumen 40 of the device 36. Since the central lumen 40 is in fluid communication with the suction aperture 24', the tissue debris is drawn through the lumen 40 and aperture 24' by the vacuum force applied to the drive-motor handle.

Figure 4:
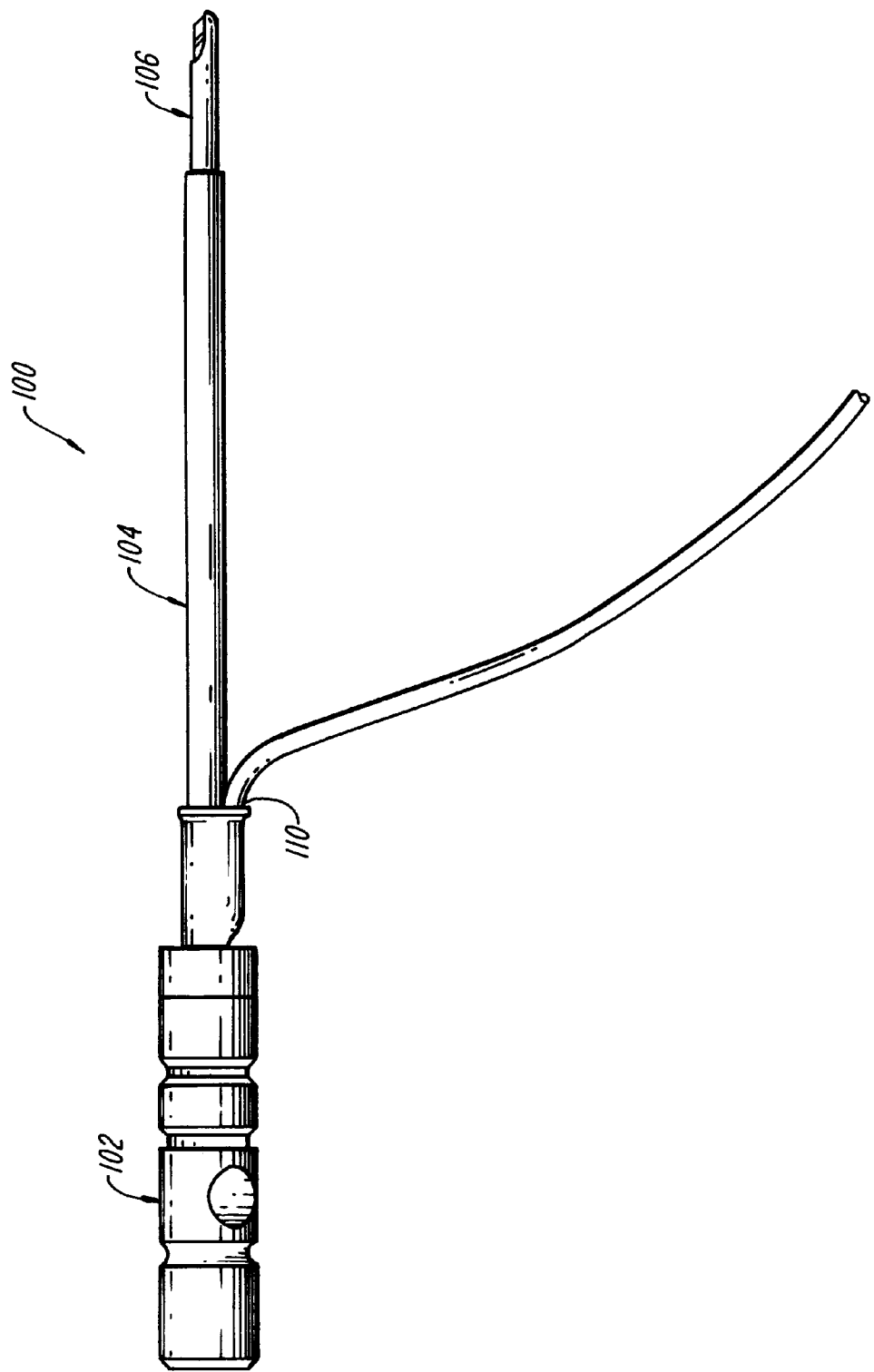
FIG. 4 is a side view of another embodiment of an electrosurgical cutting device according to the present invention.

FIG. 4 illustrates another embodiment of the rotary electrosurgical device 100 of the invention. The base 102, outer sheath 104, and tissue affecting device 106 are similar or identical to the parts described above with respect to FIGS. 1–3C which correspond to these parts. During bipolar operation, an electrical lead connected to one pole of the electrosurgical generator is connected to the outer sheath 104 through the electrical connection junction 110, and the exposed portions of the tissue affecting device 106 and the outer sheath 104 are electrically isolated from one another. Portions of the outer sheath and connection junction 110 are covered by a coating of non-conductive material to insulate the device and to ensure electrical isolation of the outer sheath and the tissue affecting device.

The illustrated rotary electrosurgical device 100 operates in a manner similar to that described above.

The foregoing rotary electrosurgical devices are adapted for use in closed surgical procedures. More specifically, the devices are adapted to be inserted within a housing of a typical closed surgery access instrument such as an arthroscope, endoscope, hysteroscope, laparoscope, or resectoscope. The rotary tissue affecting element 12, 36 of the invention can be disposed within the housing of the access instrument such that the abrading end 16B, 38C of the tissue affecting devices are able to access tissue to be treated through the cutting the cutting aperture 64 of the outer sheath 50.

Having described preferred embodiments of the invention, it will now become apparent to one of ordinary skill in the art that other embodiments incorporating the concepts herein disclosed may be used. It is felt, therefore, that these concepts should not be limited to disclosed embodiments but rather should be limited only by the spirit and scope of the appended claims. The contents of all cited references are expressly incorporated herein in their entirety.

What is claimed is:

1. An electrosurgical device comprising:
    a rotating, tissue affecting element having a proximal end and a distal, tissue contacting end having a mechanical cutting device that includes an energy delivering electrode;
    a cannula disposed about said rotating tissue affecting element, said cannula having a base portion including at least one electrically conductive contact having a first end coupled to said rotating tissue affecting element and having a second end;
    a holder to hold the proximal end of said rotating, tissue affecting element, said holder coupled to the base portion of said cannula;
    a remote electrosurgical generator having an output;
    a commutator coupled between the output of said remote electrosurgical generator and the second end of at least one of the at least one electrically conductive contacts.

2. The electrosurgical device of claim 1 wherein said rotating, tissue affecting element is provided having a shape corresponding to the shape of one of:

(a) a rotating cutting device; and (b) an arthroscopic shaving device.

3. The electrosurgical device of claim 2 wherein the proximal end of said rotating, tissue affecting element is provided as an elongate drive shaft having a shape selected to engage said holder and wherein at least one of the at least one electrically conductive contact is coupled to said elongate drive shaft.

4. The electrosurgical device of claim 3 wherein said cannula forms at least a portion of one of:

(a) an arthroscope;

(b) an endoscope;

(c) a hysteroscope;

(d) a laparoscope; and (e) a resectoscope.

5. The electrosurgical device of claim 4 wherein said rotating, tissue affecting element is provided having a quantity of a non-conductive material disposed over a surface thereof along an intermediate portion between a region of the drive shaft disposed against the at least one electrically conductive contact and the distal, tissue contacting end of said rotating, tissue affecting element to electrically isolate said rotating tissue affecting element from said cannula.

6. The electrosurgical device of claim 5 further comprising a remote ground pad and wherein the distal end of said rotating, tissue affecting element corresponds to an active, energy delivering electrode and wherein a conductive signal path may be provided by said remote ground pad being adapted to be attached to a patient's body.

7. The electrosurgical device of claim 5 further comprising at least one return electrode, each of the at least one return electrodes being disposed proximate to a distal end of the cannula adjacent to said rotating, tissue affecting element.

8. The electrosurgical device of claim 7 wherein each of said at least one return electrodes is mounted on a distal, tissue contacting edge of said cannula.

9. The electrosurgical device of claim 5 further comprising a sheath mountable over an outer surface of said cannula, wherein each of said at least one return electrodes is disposed on the distal end of said sheath.

10. An electrosurgical device comprising:

(a) a cannula having a proximal end and a distal end and a cannula lumen extending from the proximal end to the distal end, said cannula including:

(1) a base having an aperture with a longitudinal axis;

(2) an outer sheath having a proximal end coupled to said bases a distal end having a sheath aperture therein and a sheath lumen forming at least a portion of the cannula lumen, the sheath lumen extending from the proximal end of said outer sheath to the distal end of said outer sheath with a longitudinal axis of the sheath lumen aligned with the longitudinal axis of the aperture in said base;

(b) a rotatable tissue affecting element having a proximal end and a distal end, said tissue affecting element disposed through the aperture in said base and in the cannula lumen, said rotatable tissue affecting element including:

(1) a rotating shaft having a proximal end disposed in said base, a distal end disposed in the cannula lumen and a first non-conductive material disposed over predetermined regions of an outer surface of said shaft with at least a portion of the outer surface of the proximal end of said shaft being exposed through the first non-conductive material;

(2) a holder assembly securing the proximal end of said shaft; and (3) a tissue treating element disposed on the distal end of said shaft, at least a portion of an outer surface of the tissue treating element being exposed through the first non-conductive material at least a portion of the tissue treating element being exposed through the sheath aperture; and (c) a commutator electrically coupled to the first end of said shaft exposed through the first non-conductive material, the commutator including:

(1) an electrically conducting tab having a first end coupled to a first electrical contact terminal and having a second end;

(2) an electrically conductive button having a first surface in contact with the second end of said electrically conducting tab; and (3) a wire having a first portion in contact with a second surface of said button and a second portion in contact with said shaft.

11. The electrosurgical device of claim 10 further comprising:

a quantity of a non-conductive material disposed over predetermined regions of an outer surface of said outer sheath with at least a portion of the outer surface of the distal end of said outer sheath being exposed through the quantity of the non-conductive material.

12. The electrosurgical device of claim 11 wherein the distal end of said shaft is scored to expose a portion of the distal end of said shaft through the quantity of the non-conductive material.

13. The electrosurgical device of claim 11 wherein the tissue treating element disposed at the distal end of said shaft is provided having one of:

(a) a serrated edge;

(b) a burr coupled to a predetermined location of the distal end of said shaft; and (c) a dremel head.

14. The electrosurgical device of claim 11 wherein said shaft is provided as an auger bit having at least one spiral groove extending between the proximal end of said shaft and the distal end of said shaft.

15. The electrosurgical device of claim 10 further comprising:

a first electrical contact terminal having a first end coupled to said commutator and a second end; and an electrosurgical generator having a first terminal coupled to the second end of said first electrical contact terminal.

16. The electrosurgical device of claim 6 further comprising a second electrical contact terminal having a first end electrically coupled to said outer sheath and having a second end coupled to a second terminal of said electrosurgical generator.

17. The electrosurgical device of claim 10 wherein said sheath lumen and said shaft are exposed through the opening in the distal end of said outer sheath.

18. The electrosurgical device of claim 17 wherein said base is provided as having a suction aperture provided therein and wherein the sheath lumen is in fluid communication with the suction aperture.

* * * * *

UNITED STATES PATENT AND TRADEMARK OFFICE
CERTIFICATE OF CORRECTION

PATENT : 5,941,876
DATED : August 24, 1999
INVENTOR(S) : Nardella et al

It is certified that error appears in the above-identified patent and that said Letters Patent is hereby corrected as shown below:

On the title page, showing the illustrative figure should be deleted to be replaced with the attached title page.

In the drawings, sheets 1-3 should be deleted to be replaced with the correct drawing sheets 1-3, consisting of Figures 1, 1A, 2, 2A, 3A, 3B and 3C, as shown on the attached pages.

Signed and Sealed this

Thirteenth Day of February, 2001

*Attest:*

NICHOLAS P. GODICI

*Attesting Officer*  Acting Director of the United States Patent and Trademark Office

United States Patent [19]
Nardella et al.

[11] Patent Number: 5,941,876
[45] Date of Patent: Aug. 24, 1999

[54] ELECTROSURGICAL ROTATING CUTTING DEVICE

[75] Inventors: Paul C. Nardella, Wareham; John F. Cvinar, Winchester; Thomas A. Wrublewski, Sharon, all of Mass.

[73] Assignee: Medical Scientific, Inc., Taunton, Mass.

[21] Appl. No.: 08/803,170

[22] Filed: Feb. 19, 1997

Related U.S. Application Data

[60] Provisional application No. 60/013,251, Mar. 11, 1996.
[51] Int. Cl.⁶ .................................................. A61B 17/32
[52] U.S. Cl. ........................... 606/45; 606/49; 606/170; 606/180; 604/22
[58] Field of Search ..................... 606/41, 42, 45–50, 606/170, 180; 604/21, 22

[56] References Cited

U.S. PATENT DOCUMENTS

| | | |
|---|---|---|
| 3,945,375 | 3/1976 | Banko. |
| 4,016,881 | 4/1977 | Rioux et al. |
| 4,532,924 | 8/1985 | Auth et al. |
| 4,637,390 | 1/1987 | Sorochenko. |
| 4,657,017 | 4/1987 | Sorochenko. |
| 4,674,499 | 6/1987 | Pao. |
| 4,802,476 | 2/1989 | Noerenberg et al. |
| 4,842,578 | 6/1989 | Johnson et al. |
| 4,917,082 | 4/1990 | Grossi et al. |
| 5,037,379 | 8/1991 | Clayman et al. |
| 5,047,027 | 9/1991 | Rydell. |
| 5,080,660 | 1/1992 | Buelna. |
| 5,122,138 | 6/1992 | Manwaring. |
| 5,133,713 | 7/1992 | Huang et al. |
| 5,176,677 | 1/1993 | Wuchinich. |
| 5,192,280 | 3/1993 | Parins. |
| 5,197,964 | 3/1993 | Parins. |
| 5,201,731 | 4/1993 | Hakky. |
| 5,217,458 | 6/1993 | Parins. |
| 5,217,478 | 6/1993 | Rexroth. |
| 5,269,780 | 12/1993 | Roos. |
| 5,269,782 | 12/1993 | Sutter. |
| 5,269,794 | 12/1993 | Rexroth. |
| 5,282,799 | 2/1994 | Rydell. |
| 5,290,282 | 3/1994 | Casscells. |
| 5,290,303 | 3/1994 | Pingleton et al. |
| 5,304,124 | 4/1994 | Essig et al. |
| 5,318,564 | 6/1994 | Eggers. |
| 5,318,589 | 6/1994 | Lichtman. |
| 5,324,289 | 6/1994 | Eggers. |
| 5,330,471 | 7/1994 | Eggers. |
| 5,364,395 | 11/1994 | West, Jr. |
| 5,391,166 | 2/1995 | Eggers. |
| 5,403,312 | 4/1995 | Yates et al. |
| 5,411,514 | 5/1995 | Fucci et al. |
| 5,423,844 | 6/1995 | Miller .................. 606/171 |
| 5,441,499 | 8/1995 | Fritzsch. |
| 5,445,638 | 8/1995 | Rydell et al. |
| 5,456,689 | 10/1995 | Kresch et al. |
| 5,480,397 | 1/1996 | Eggers et al. |
| 5,484,435 | 1/1996 | Fleenor et al. |
| 5,492,527 | 2/1996 | Glowa et al. |
| 5,527,331 | 6/1996 | Kresch et al. |
| 5,531,677 | 7/1996 | Lundquist et al. |
| 5,569,244 | 10/1996 | Hahnen. |
| 5,571,100 | 11/1996 | Goble et al. |
| 5,697,281 | 12/1997 | Eggers et al. |
| 5,697,536 | 12/1997 | Eggers et al. |
| 5,697,882 | 12/1997 | Eggers et al. |
| 5,697,909 | 12/1997 | Eggers et al. |

FOREIGN PATENT DOCUMENTS

| | | |
|---|---|---|
| 0596436 A1 | 5/1994 | European Pat. Off. |
| 9611638 | 4/1996 | WIPO. |
| 9624296 | 8/1996 | WIPO. |

*Primary Examiner*—Michael Peffley
*Attorney, Agent, or Firm*—Nutter, McClennen & Fish, LLP

[57] ABSTRACT

An electrosurgical apparatus includes a rotary, tissue affecting device in the form of one or more rotating blades, a rotating drill, or a rotating shaving/abrading device that serves as an active, energy delivering electrode. The active electrode effectively cuts tissue at the surgical site without relying solely upon the mechanical cutting action of the tissue affecting device. The rotary surgical device can be in a form such that it is suitable for use in open or closed surgery.

18 Claims, 4 Drawing Sheets

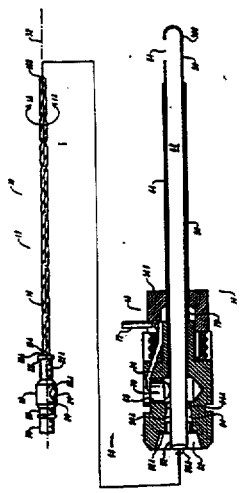

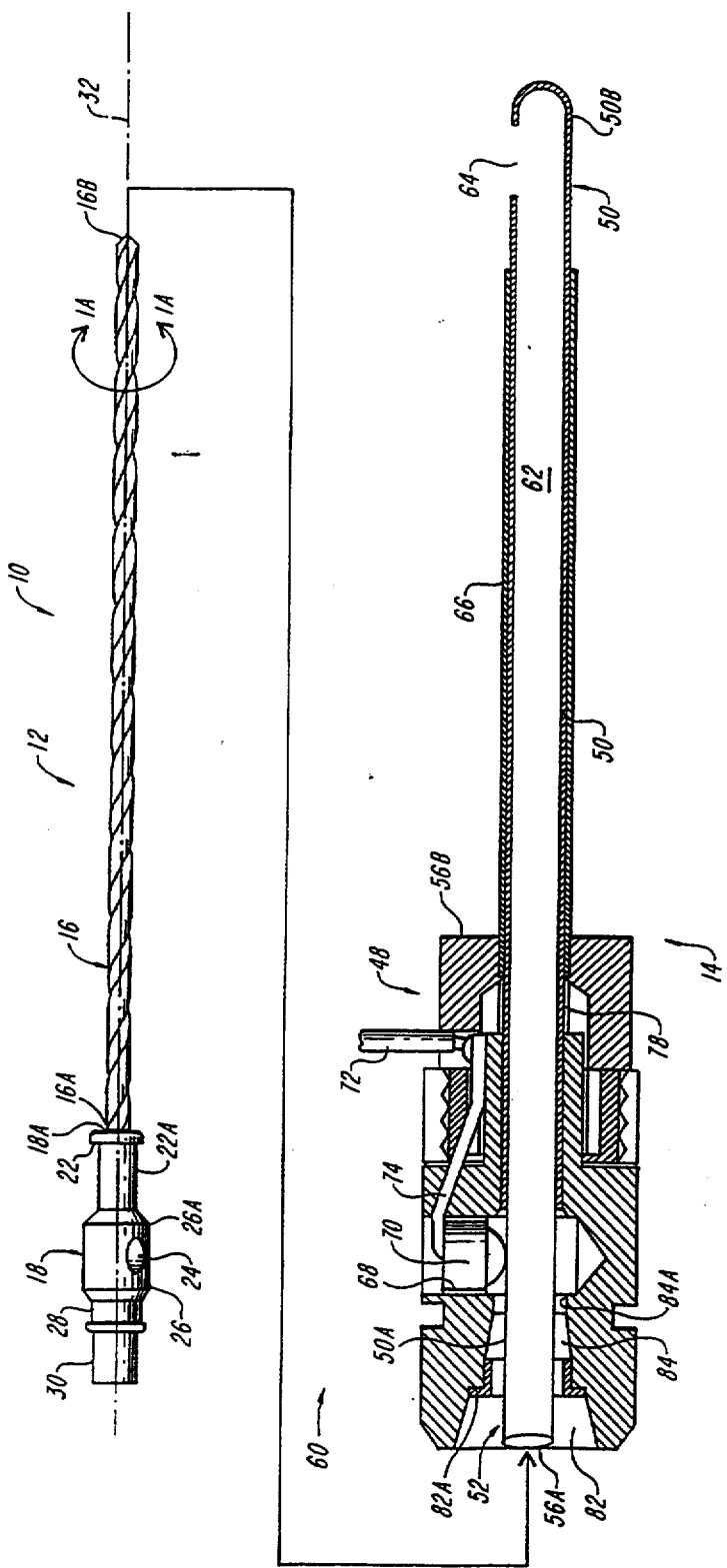
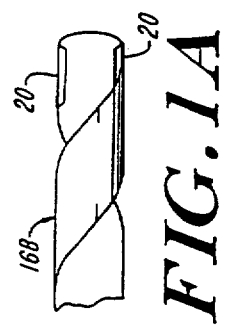
FIG. 1
FIG. 1A

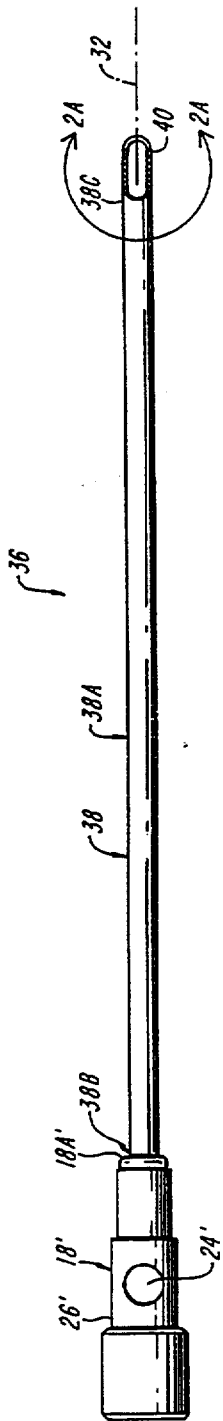
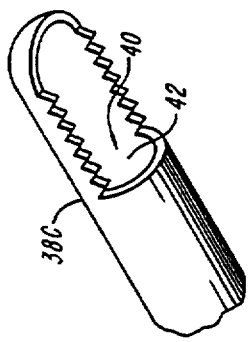
FIG. 2
FIG. 2A